United States Patent
Zhang

(10) Patent No.: US 11,504,040 B2
(45) Date of Patent: Nov. 22, 2022

(54) WEARABLE HEART MONITORING DEVICE, HEART MONITORING SYSTEM AND METHOD

(71) Applicant: INVENTEC APPLIANCES (JIANGNING) CORPORATION, Nanjing (CN)

(72) Inventor: Su Zhang, Nanjing (CN)

(73) Assignee: INVENTEC APPLIANCES (JIANGNING) CORPORATION, Jiangsu (CN)

( * ) Notice: Subject to any disclaimer, the term of this patent is extended or adjusted under 35 U.S.C. 154(b) by 795 days.

(21) Appl. No.: 16/475,148

(22) PCT Filed: Dec. 30, 2016

(86) PCT No.: PCT/CN2016/113573
§ 371 (c)(1),
(2) Date: Jul. 1, 2019

(87) PCT Pub. No.: WO2018/120049
PCT Pub. Date: Jul. 5, 2018

(65) Prior Publication Data
US 2019/0328253 A1  Oct. 31, 2019

(51) Int. Cl.
*A61B 5/25* (2021.01)
*A61B 5/0245* (2006.01)
*A61B 5/00* (2006.01)

(52) U.S. Cl.
CPC ............ *A61B 5/25* (2021.01); *A61B 5/0245* (2013.01); *A61B 5/0006* (2013.01);
(Continued)

(58) Field of Classification Search
CPC ....... A61B 5/25; A61B 5/0245; A61B 5/0006; A61B 5/0059; A61B 5/6802; A61B 5/6823; A61B 5/318
See application file for complete search history.

(56) References Cited

U.S. PATENT DOCUMENTS

| 4,635,646 A | 1/1987 | Gilles et al. |
| 2008/0091090 A1 | 4/2008 | Guillory et al. |

(Continued)

FOREIGN PATENT DOCUMENTS

| CN | 1110121 A | 10/1995 |
| CN | 201379569 Y | 1/2010 |

(Continued)

OTHER PUBLICATIONS

Notice of Allowance dated Aug. 13, 2021 of Chinese Patent No. 201680003494.6.
(Continued)

*Primary Examiner* — Jung Kim
(74) *Attorney, Agent, or Firm* — Qinghong Xu

(57) ABSTRACT

A wearable cardiac monitoring device comprises a processor; a electrocardiogram (ECG) signal collecting unit; a photoelectric signal collecting unit; and a power source configured to provide power to the processor, the ECG signal collecting unit and the photoelectric signal collecting unit simultaneously; wherein the processor determines whether the current mode is at a ECG collecting mode or a photoelectric collecting mode; wherein the ECG signal collecting unit collects user's ECG signals in the ECG collecting mode, and the photoelectric signal collecting unit collects photoelectric signals of the user's measured part under the illumination of light.

16 Claims, 15 Drawing Sheets

(52) U.S. Cl.
CPC ........... *A61B 5/0059* (2013.01); *A61B 5/6802* (2013.01); *A61B 5/6823* (2013.01)

(56) References Cited

U.S. PATENT DOCUMENTS

| | | | |
|---|---|---|---|
| 2014/0107493 | A1 | 4/2014 | Yuen et al. |
| 2014/0235978 | A1 | 8/2014 | Banet et al. |
| 2016/0192856 | A1 | 7/2016 | Lee |
| 2017/0055845 | A1* | 3/2017 | Mirov .................... A61B 5/316 |

FOREIGN PATENT DOCUMENTS

| | | | |
|---|---|---|---|
| CN | 102038549 | A | 5/2011 |
| CN | 103536286 | A | 1/2014 |
| CN | 103876726 | A | 6/2014 |
| CN | 103919538 | A | 7/2014 |
| CN | 104207756 | A | 12/2014 |
| CN | 104273808 | A | 1/2015 |
| CN | 104510463 | A | 4/2015 |
| CN | 104602592 | A | 5/2015 |
| CN | 104662580 | A | 5/2015 |
| CN | 104688202 | A | 6/2015 |
| CN | 104812296 | A | 7/2015 |
| CN | 105310686 | A | 2/2016 |
| CN | 205106600 | U | 3/2016 |
| CN | 105518626 | A | 4/2016 |
| CN | 211749856 | U | 10/2020 |
| KR | 20040072553 | A | 8/2004 |
| TW | 201012432 | A | 4/2010 |
| TW | 201208648 | A | 3/2012 |
| TW | 201540260 | A | 11/2015 |
| WO | 2016195347 | A1 | 12/2016 |

OTHER PUBLICATIONS

International Search Report for PCT application No. PCT/CN2016/113573 dated Sep. 28, 2017.
The 1st Office Action dated Jan. 6, 2021 from CN 201680003494.6.
The 1st Office Action dated Aug. 31, 2018 from TW 106144591.

* cited by examiner

WEARABLE HEART MONITORING DEVICE, HEART MONITORING SYSTEM AND METHOD

CROSS REFERENCE

This application is based upon and claims the benefit of priority of Chinese Patent Applications No. 201680003494.6, filed on Dec. 30, 2016, the entire contents thereof are incorporated herein by reference.

TECHNICAL FIELD

The invention relates to the technical field of health monitoring, in particular to a wearable cardiac monitoring device, a cardiac monitoring system and a method thereof for monitoring cardiac status in real time and being easy to wear.

BACKGROUND

Cardiovascular disease is one of the major virulence factors, and the incidence of sudden cardiac death has increased in recent years. Therefore, the detection of cardiac status is important for the early detection of heart disease. At present, people usually use electrocardiogram (ECG) to perform ECG signal detection in hospitals. It is necessary to paste multiple measurement electrodes on the human skin. The measurement steps are complicated, and the characteristics of ECG signals can only be observed and detected at a certain moment. However, the syndrome of some heart diseases in the human body is not always presented. Sometimes the syndrome of some heart diseases in human body may not be discovered by timely performing the ECG measurements in hospitals. Many people suffer heart disease without being aware of the syndrome of it. Heart disease becomes a hidden killer of health.

In order to enable the monitoring of cardiac status at any time, the following two techniques are mainly proposed in the prior art:

(1) One is to adopt a dynamic electrocardiogram device. Dynamic electrocardiogram is a method that can continuously record and compile ECG changes in the active and quiet state of the human heart for a long time. However, the existing dynamic electrocardiogram device is large in size and very inconvenient to carry, and is a great burden for users who wear the dynamic electrocardiogram device. The user has to use this method when the user feels uncomfortable. Moreover, the dynamic electrocardiogram device only dynamically collects the user's ECG signal, and cannot perform real-time analysis. The specific analysis is not a real time result since the analysis still needs to be provided by the doctor after doctor's diagnosis in the hospital.

(2) Some portable heart rate detecting devices are also disclosed in the prior art. For example, adding a photoelectrical heart rate measuring device in a smart wristband, but this method is greatly affected by the light and other interferences of the surrounding environment. The measurement of the prior art is not quite accurate to be an accurate basis for disease diagnosis.

SUMMARY

In view of the problems in the prior art, an object of the present disclosure is to provide a wearable cardiac monitoring device, a cardiac monitoring system and a method thereof, which adopt electrocardiogram (ECG) and photoelectric for monitoring cardiac status. The features disclosed by the present disclosure are integrated in a wearable part with high accuracy of cardiac detection and easy wormed.

One embodiment of the present disclosure provides a wearable cardiac monitoring device including a processor; a electrocardiogram (ECG) signal collecting unit; a photoelectric signal collecting unit; and a power source configured to provide power to the processor, the ECG signal collecting unit and the photoelectric signal collecting unit simultaneously; wherein the processor determines whether the current mode is at a ECG collecting mode or a photoelectric collecting mode; wherein the ECG signal collecting unit collects user's ECG signals in the ECG collecting mode, and the photoelectric signal collecting unit collects photoelectric signals of the user's measured part under the illumination of light.

One embodiment of the present disclosure provides a cardiac monitoring system, comprising a wearable cardiac monitoring device and a data analysis platform. The wearable cardiac monitoring comprises a processor; an electrocardiogram (ECG) signal collecting unit; a photoelectric signal collecting unit; and a power source configured to provide power to the processor, the ECG signal collecting unit and the photoelectric signal collecting unit simultaneously; wherein the processor determines whether the current mode is at a ECG collecting mode or a photoelectric collecting mode; wherein the ECG signal collecting unit collects user's ECG signals in the ECG collecting mode, and the photoelectric signal collecting unit collects photoelectric signals of the user's measured part under the illumination of light. The data analysis platform is configured to generate cardiac state parameters in response to the ECG signal and/or the photoelectric signal.

The embodiment of the invention further provides a cardiac monitoring method, implemented by a cardiac monitoring system. The cardiac monitoring system comprises a wearable cardiac monitoring device and a data analysis platform. The wearable cardiac monitoring comprises a processor; an electrocardiogram (ECG) signal collecting unit; a photoelectric signal collecting unit; and a power source configured to provide power to the processor, the ECG signal collecting unit and the photoelectric signal collecting unit simultaneously; wherein the processor determines whether the current mode is at a ECG collecting mode or a photoelectric collecting mode; wherein the ECG signal collecting unit collects user's ECG signals in the ECG collecting mode, and the photoelectric signal collecting unit collects photoelectric signals of the user's measured part under the illumination of light. The data analysis platform is configured to generate cardiac state parameters in response to the ECG signal and/or the photoelectric signal. The cardiac monitoring method comprises the following steps: determining whether the current mode is in a ECG collecting mode or a photoelectric collecting mode; collecting user's ECG signals in the ECG collecting mode; collecting photoelectric signals of user's measured part irradiated by light in the photoelectric collecting mode; generating cardiac state parameters in response to the collected ECG signals and/or the collected photoelectric signals.

The wearable cardiac monitoring device, cardiac monitoring system and method provided by the present disclosure have the following advantages:

The present disclosure provides a technical solution for monitoring the cardiac status real time and being easy to wear. The technical solution is implemented in a combination with electrocardiogram and photoelectric method for performing cardiac status monitoring. The electrocardiogram monitoring has high accuracy, and the photoelectric monitoring has a fast speed. Various cardiac monitoring methods are selected according to the need. The device has both advantages of accuracy and real-time. The device is integrated in the wearing parts. The size of the device is compact. The device is easy to wear. The device can execute the cardiac monitoring anytime and anywhere, without bringing the carrying burden of users, and improve user's usage experience.

BRIEF DESCRIPTION OF THE DRAWINGS

By reading the detailed description of the non-limiting embodiments with reference to the following drawings, other features, purposes and advantages of the present disclosure will become more apparent.

DETAILED DESCRIPTION

Figure 1:
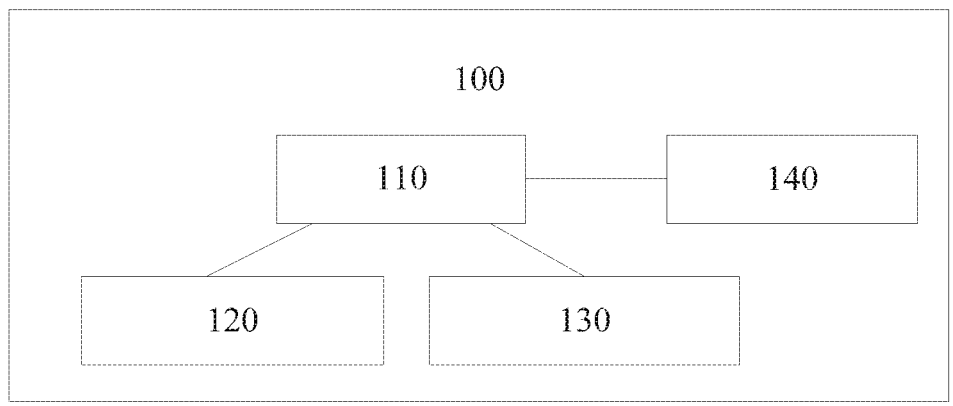
FIG. 1 is a block diagram of a wearable cardiac monitoring device of one embodiment of the present disclosure.

The example embodiments will now be described more fully with reference to the accompanying drawings. However, the example embodiments can be implemented in a variety of forms and should not be construed as being limited to the embodiments described herein; on the contrary, the provision of these embodiments enables the invention to be comprehensive and complete and to convey the concept of the example embodiments comprehensively to those skilled in the art. The same reference numerals in the figure represent the same or similar structures, and therefore duplicate descriptions of them will be omitted.

As shown in FIG. 1, one embodiment of the present disclosure provides a wearable cardiac monitoring device 100. The wearable cardiac monitoring device 100 includes a processor 110, an electrocardiogram (ECG) signal collecting unit 120, a photoelectric signal collecting unit 130, and a power source 140. The power source 140 is configured to simultaneously provide power to the processor 110, the ECG signal collecting unit 120, the photoelectric signal collecting unit 130 and the power source 140. The processor 110 is configured to determine whether the current mode is at a ECG collecting mode or a photoelectric collecting mode. The ECG signal collecting unit 120 is configured to collect user's ECG signals in the ECG collecting mode, and the photoelectric signal collecting unit 130 is configured to collect photoelectric signals of the user's measured part under the illumination of light.

Therefore, the present disclosure adopts ECG and photoelectric methods for cardiac status monitoring due to ECG monitoring having advantages of high accuracy and photoelectric monitoring having advantages of a faster speed. Various cardiac monitoring methods are selected according to the needs. The processor 110, the ECG signal collecting unit 120, the photoelectric signal collecting unit 130 and the power source 140 are installed in a portable device worn by the user, which is easy to use, and the portable device can perform cardiac monitoring at any time. The device with the cardiac monitoring function of the present disclosure has both accuracy and real-time effects in cardiac monitoring.

The ECG signal generally includes cardiac current data. Before the heart start to beat, the myocardium firstly excites, and then produces a weak current, a cardiac current, during the excitement. The current is transmitted through the body tissue to the various parts of the body. Since the tissues of different parts of the body are different, the distance between the parts and the heart is different. Thus, different potential changes are presented in various parts of the human body surface. Therefore, the cardiac current is measurable by collecting the potential of different parts of the human body.

Figure 2:
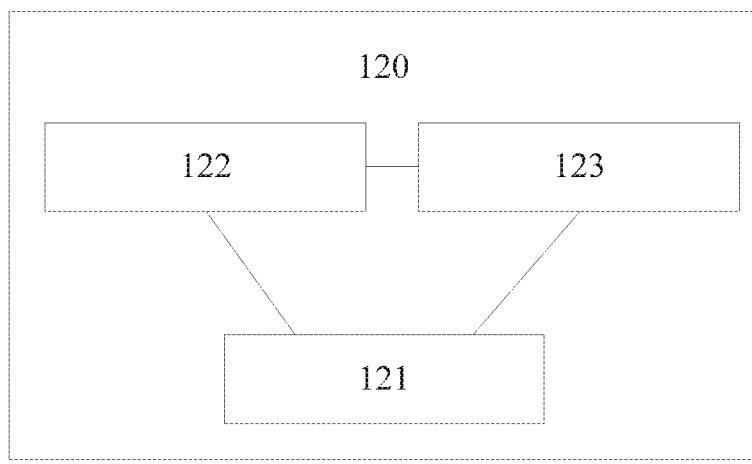
FIG. 2 is a block diagram of an ECG signal collecting unit of one embodiment of the present disclosure.

As shown in FIG. 2, in one embodiment of the present disclosure, a ECG signal collecting unit 120 includes a first electrode 121, a second electrode 122, and a third electrode 123. The first electrode 121 is close to the user's heart. The second electrode 122 and third electrode 123 are close to user's skin during the ECG collecting mode, wherein the first electrode 121, the second electrode 122 and the third electrode 123 are formed a cardiac current measuring circuit. The measurement of cardiac current is more accurate than the measurement of photoelectric mode, but the measurement of cardiac current requires a certain continuous measurement time.

The second electrode 122 and the third electrode 123 are symmetrically disposed with respect to the first electrode 121, so that the potential of the user's body can be measured, thereby obtaining cardiac current data.

Figure 3:
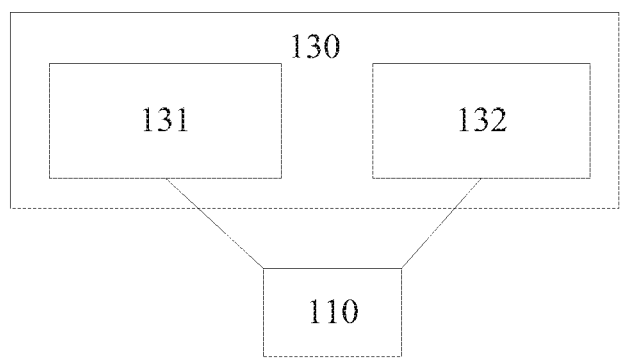
FIG. 3 is a block diagram of an optical signal collecting unit of one embodiment of the present disclosure.

As shown in FIG. 3, FIG. 3 is a schematic diagram of a photoelectric signal collecting unit of one embodiment of the present disclosure. In the photoelectric collecting mode, the photoelectric signal collecting unit 130 is close to the user's skin. The photoelectric signal collecting unit 130 includes a light emitter 131 configured for emitting light to surface of user's skin; and a photosensitive receiver 132 is configured for receiving the reflected light reflected by the user's measured part. In the photoelectric collecting mode, the processor 110 controls the light emitter 131 to emit light to the user's skin, for example, to emit red light to the user's skin. During the heart beating period, the blood hemoglobin in blood vessels has different absorbance to red light. Therefore, the reflected light reflected by the skin is different. The reflected light is received by the photosensitive receiver 132. The change of the reflected light presents the change of the heart rate.

The method of photoelectric measurement is fast and can meet the requirements of timeliness, but it is easily interfered by external light, cleanliness of user's skin and other factors. The measurement is not accurate enough. Therefore, the present disclosure combines this mode with the method of ECG measurement, and different measurement modes can be selected according to needs. When more accurate measurement data is needed, the ECG measurement mode is kept functioning. When heart rate data needs to be obtained immediately, photoelectric measurement mode is then entered.

The manner of photoelectric measurement listed herein is only a preferred embodiment. In practice, it is also possible to use the light emitter 131 to emit green light to user's skin. The photosensitive receiver 132 receives the transmitted light of the skin, and the blood in the blood vessel changes in density during pulsating which is causing a change in light transmittance. The change in transmitted light received by the photosensitive receiver 132 can presents the change of the heart rate. The photosensitive receiver 132 receives the reflected light. The light emitter 131 and the photosensitive receiver 132 can be disposed on the same side of the user's skin, and the green light is configured to measure with high accuracy.

Figure 4:
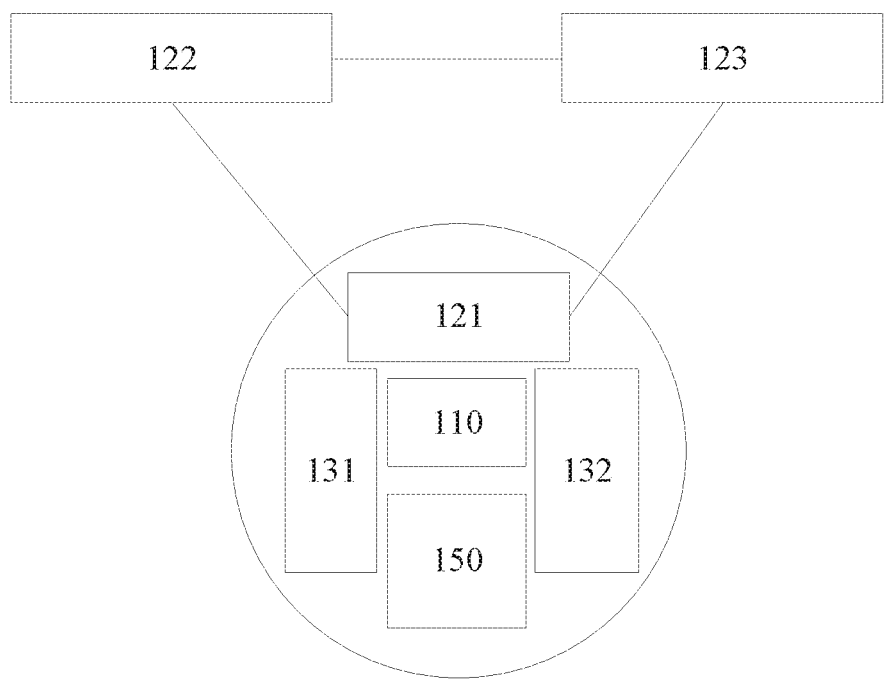
FIG. 4 is a block diagram of a wearable cardiac monitoring device with data transmission function according to the present disclosure.

As shown in FIG. 4, the wearable cardiac monitoring device of the present disclosure further comprises a wireless transmission unit 150 configured to send the ECG signal and/or the photoelectric signal to a data analysis platform. The data analysis platform generates cardiac state parameters in response to the ECG signal and/or the photoelectric signal. Therefore, the detection of the electrocardiographic signal and/or the photoelectric signal is performed, and the electrocardiographic signal and/or the photoelectric signal are also sent to the external data analysis platform through the wireless transmission unit 150. The wearable cardiac monitoring device receives the cardiac state parameters which are analyzed by the data analysis platform.

The cardiac state parameters include electrocardiogram index data and heart rate. When the ECG signal collecting unit collects the ECG signal, the data analysis platform may draw an electrocardiogram in response to the collected ECG signal and calculate various indicators, such as the P-wave time, P-wave amplitude, P-wave shape and the P-R cycle time of the electrocardiogram. When the photoelectric signal collecting unit collects the photoelectric signal, the data analysis platform can obtain the user's heart rate in response to the collected photoelectric signal.

Further, the processor 110 is configured to convert the ECG signal into a digital signal after the ECG signal is filtered and amplified by the processor 110. The processor 110 is further configured to convert the photoelectric signal into a digital signal after the photoelectric signal is filtered and amplified by the processor 110.

After the processor 110 receives the digital signal, the wireless transmission unit 150 sends the digital signal corresponding to the ECG signal and the digital signal corresponding to the photoelectric signal to the data analysis platform. If the processor 110 does not perform preliminary data processing, the wireless transmission unit 150 directly sends the ECG signal and the photoelectric signal to the data analysis platform. The data analysis platform uniformly performs data processing and data analysis.

Figure 5:
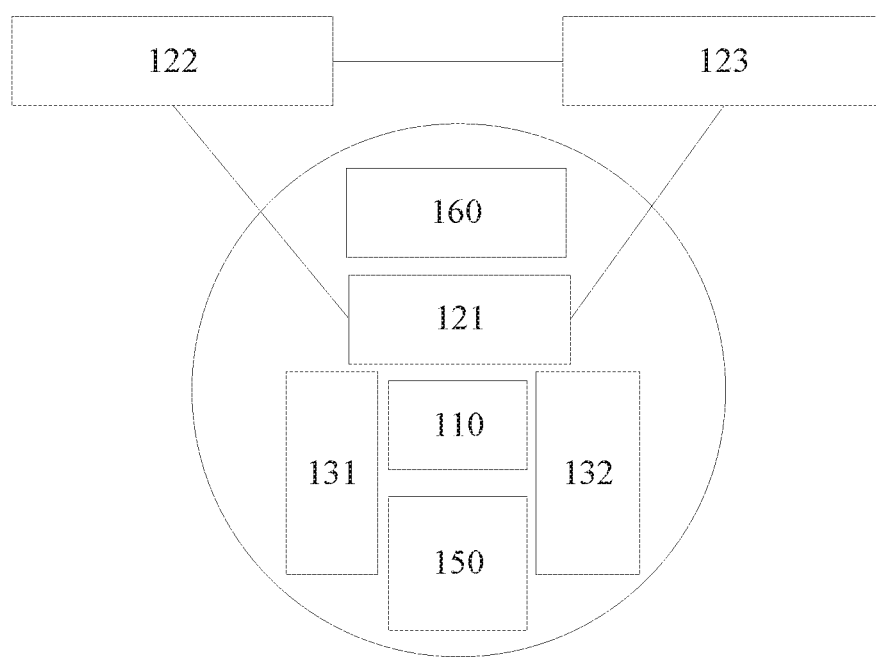
FIG. 5 is a block diagram of a wearable cardiac monitoring device with alarm function.

As shown in FIG. 5, the wearable cardiac monitoring device of the present disclosure may further include an alarm unit 160. The alarm unit 160 is configured to push an alarm signal to the user when the cardiac monitoring device receives the abnormal notification of the cardiac state parameters transmitted by the data analysis platform. The alarm unit 160 pushes the alarm signal in ways of an audible alarm, an optical alarm or an acousto-optic alarm. Therefore, in the the process of real-time monitoring of the cardiac status, once an abnormal situation is occurred, the abnormal situation reaches the user in time to avoid the time latency in delivering the abnormal notification of cardiac status monitoring and achieve early detection of heart disease.

When the data analysis platform receives the ECG signal of the user, the data analysis platform analyzes the received ECG signal to obtain the ECG index data. If the ECG index data is abnormal, the heart is determined as abnormal. For example, when the P-R period is prolonged, it may indicate ventricular hypertrophy and indoor conduction. ST-segment depression may indicate myocardial ischemia. ST-segment elevation may indicate acute conditions such as acute myocardial infarction. When the data analysis platform receives the user's ECG signal, the data analysis platform analyzes the received ECG signal to obtain the user's heart rate. If the heart rate is too fast or too slow, it may also indicate that the heart is abnormal, and it is necessary to promptly report the alarm through the alarm unit 160.

Figure 6:
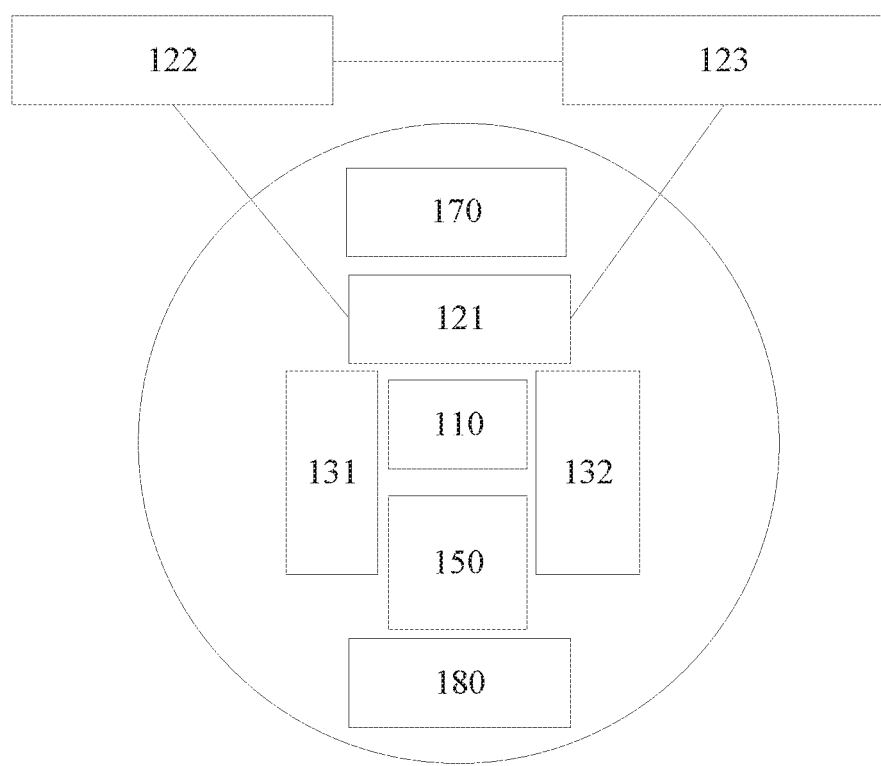
FIG. 6 is a block diagram of a wearable cardiac monitoring device with locating function according to the present disclosure.

As shown in FIG. 6, the wearable cardiac monitoring device of the present disclosure may further include a locating unit 170 configured to automatically locate user's position information. When the cardiac monitoring device receives the abnormal notification of cardiac state, the locating unit 170 transmits the user's position information to the external data analysis platform. Further, the wearable cardiac monitoring device of the present disclosure may further include a display unit 180 and a user information input unit. The user information input unit is configured to obtain the user's action capability confirmation information.

When the processor 110 receives an abnormality notification of the cardiac state parameter, the user is firstly required to confirm whether the user still have action capability. If the user's action capability confirmation is received within a predetermined time, it may indicate that the user still has the action and consciousness capability. At this time, the locating unit 170 obtains the user's position information and sends it to the data analysis platform. The data analysis platform matches the most nearby medical institution, and transmits the matched medical institution information to the processor 110. The processor 110 controls the display unit 180 to display the matched medical institution information. When the user sees the most nearby medical institution, the user can go to the most nearby medical institution for medical treatment.

If the user's action capability confirmation is not received within the predetermined time, it may indicate that the user may not have the action or consciousness capability. The location unit 170 obtains the user's position information and sends it to the data analysis platform. After the data analysis platform matches the most nearby medical institution, the data analysis platform will send the user's position information and cardiac state parameters to the matched medical institution, and asks the medical institution to send rescuers to the designated location to perform the rescue operation, which will avoid the delay caused by the user's inability to go to the hospital for medical treatment, and greatly guarantee the safety of the user.

The processor 110, the ECG signal collecting unit 120, the photoelectric signal collecting unit 130, and the power source 140 are all installed in a wearable part. The user can wear the wearable part on a corresponding part of the body. Therefore, the wearable cardiac monitoring device of the present disclosure is very easy to wear, and does not become a burden of user in using the wearable cardiac monitoring device and improves the user experience.

Figure 7:
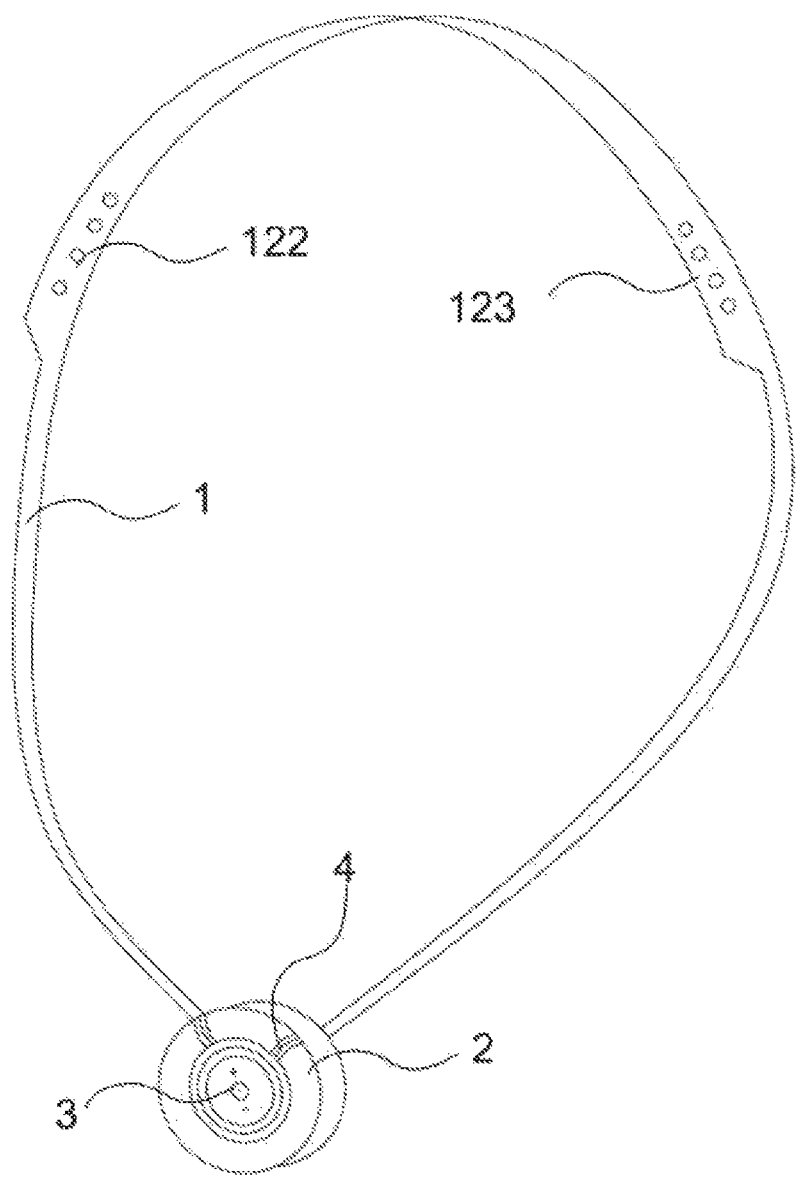
FIG. 7 is a schematic view of a wearable cardiac monitoring device of one embodiment of the present disclosure.

As shown in FIG. 7, the wearable part includes an annular ring. The first electrode 121, the second electrode 122, and the third electrode 123 are disposed on the annular ring. In this embodiment, the first electrode 121 is disposed at a first position of the annular ring, and the second electrode 122 and the third electrode 123 are disposed at second position and third position of the annular ring respectively. The second position and third position are respectively distant from the first position with a same distance.

Figure 8:
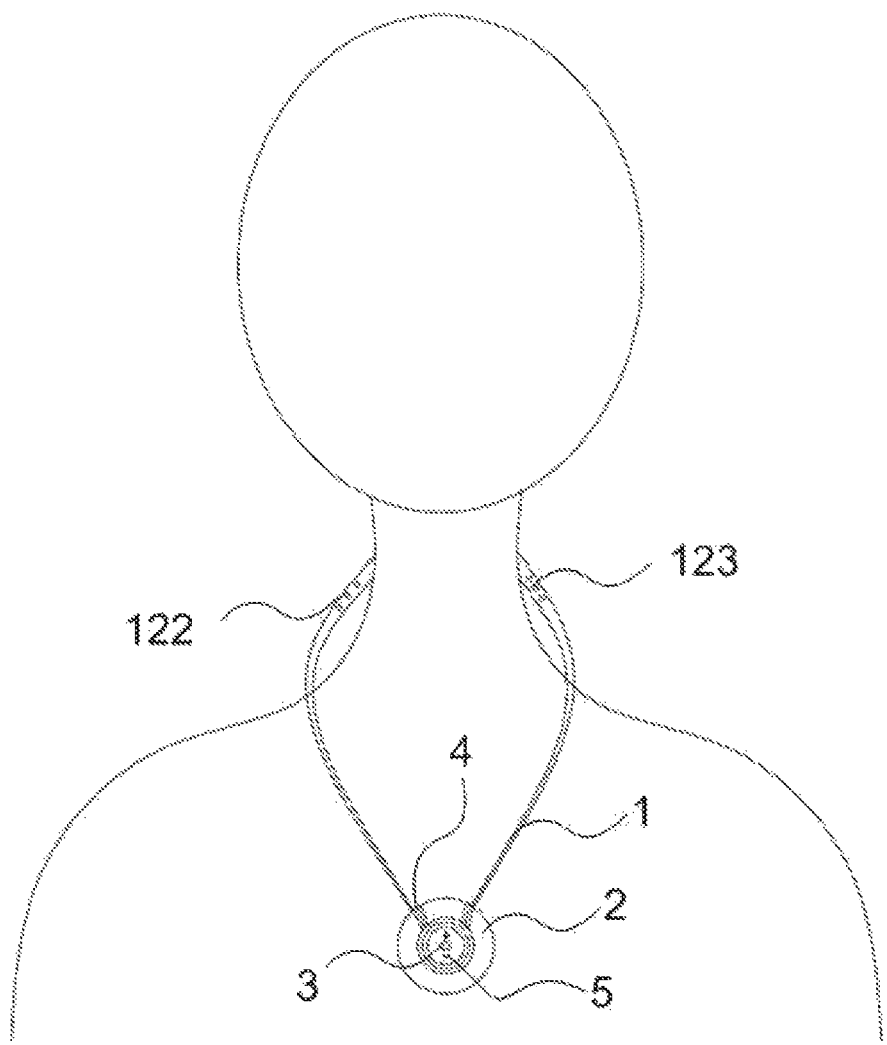
FIG. 8 is a schematic view of a necklace cardiac monitoring device of one embodiment of the present disclosure.

As shown in FIG. 8, the annular ring includes a necklace rope 1, and a conductive ring is disposed in the necklace rope 1. The necklace rope 1 is also connected to a pendant 2. The first electrode 121, the photoelectric signal collecting unit 130 and the processor 110 are all installed in the pendant 2. The first electrode 121 is electrically connected to the second electrode 122 and the third electrode 123 via the conductive ring. When the user wears the necklace rope 1, the second electrode 122 and the third electrode 123 are respectively close to a side of the user's neck. In the ECG collecting mode, the pendant 2 is close to the user's heart position.

In this embodiment, the speaker 4 is also provided as an alarm unit on the pendant 2. When an abnormality appears in the cardiac state parameters, an alarm signal is issued in time to alert the user.

Furthermore, a position adjustment button 5 is disposed at a position where the necklace rope 1 is connected to the pendant 2. The length of the necklace rope 1 is adjustable when the length adjustment button 5 is at an adjusted state. For example, a torsion spring may be disposed at a position where the necklace rope 1 and the pendant 2 are connected. When the length adjustment button 5 is pressed, the torsion spring is loosened by a transmission mechanism, such that the length of the necklace rope 1 is then adjusted. When the length adjustment button 5 is released, the pressure on the torsion spring is restored, such that the length of the necklace lanyard 1 is fixed. At the photoelectric collection mode, since the pendant 2 is placed close to the user's skin instead of close to the user's heart. The user adjusts the length of the necklace rope 1 for comfort or good looking, when the ECG collecting mode is not used. The necklace lanyard 1 needs to be adjusted such that that the pendant 2 is placed close to the user's heart during the ECG collecting mode.

Further, a mode selection button 3 is further disposed in the pendant 2. When the mode selection button 3 is switched to a first mode and the first mode is detected by the processor 110, the ECG collecting mode is then determined by the processor 110. When the mode selection button 3 is switched to a second mode and the second mode is detected by the processor 110, the photoelectric collecting mode is then determined by the processor 110. In some embodiments, the mode selection button 3 is switchable in three states and the three states are respectively corresponding to three different working modes, which are shown in the following table 1.

TABLE 1

| Mode selection button status and working mode correspondence table | | | |
| --- | --- | --- | --- |
| Mode selection button status | first mode | second mode | third mode |
| Working mode | ECG collecting mode | photoelectric collecting mode | off mode |

In usage of the device, the default working mode of the wearable cardiac monitoring device is set at the ECG collecting mode, which means the cardiac current signal is collected by three electrodes in real time. When the user needs to obtain the heart rate right away, the mode selection button is pressed to switch to the second mode, which means the wearable cardiac monitoring device enters the photoelectric collecting mode. The processor 110 controls the photoelectric signal collecting unit 130 to perform the photoelectric signal collection to quickly obtain the heart rate signals.

Further, the working mode of the wearable cardiac monitoring device is selected based on the power capacity detection of the power source 140. When the power capacity of the power source 140 is less than the second pre-defined threshold, the sleep state is then automatically activated for reducing the power consumption and prolonging the use time of the wearable cardiac monitoring device. When the user needs to switch to the photoelectric collecting mode or the ECG collecting mode, the wearable cardiac monitoring device is activated via operating the mode selection button 3. Before entering the sleep mode, the processor 110 further obtains the cardiac state parameter analysis result of the data analysis platform. If the cardiac state parameter analysis result is normal during the predetermined time period, the sleep state is then activated by the processor. If the abnormality of the cardiac state parameter analysis result in the predetermined time period is appeared, the sleep state is not activated. The cardiac state monitoring will be continued to avoid the user's unexpected situations.

When the power capacity of the power source 140 is greater than the second pre-defined threshold and less than the first pre-defined threshold, if current mode is at the ECG collecting mode, the processor 110 may control to switch to the photoelectric collecting mode, and set the photoelectric signal collection interval period. For example, The photoelectric signal is hourly measured, or the photoelectric signal is measured every half of an hour. The reason for this is that the ECG signals are continuously collected during ECG collecting mode. The power consumption is then relatively large. After a long time interval, the photoelectric signals are quickly collected and results are quickly generated. Compared with ECG collecting, photoelectric signal collecting saves more energy. Therefore, when the battery capacity is low, the wearable cardiac monitoring device is switched to the photoelectric collecting mode and the monitoring is performed via the photoelectric collecting mode.

In this embodiment, a necklace is used as a carrier of the processor 110, the ECG signal collecting unit 120, and the photoelectric signal collecting unit 130. The second electrode 122 and the third electrode 123 are disposed close to the neck. When the user wearing a necklace, the natural shape of the necklace provides a number of portions which directly touch the skin of the human body. Since the overall size of the necklace is relatively compact, the user will not have any discomfort when wearing the necklace. It is even possible to add ornaments to the necklace to make the necklace play as an ornament, and the necklace is easy to carry and easy to perform the detection at any time.

The wearable cardiac monitoring device of the present disclosure further comprises a cardiac state parameter pushing unit for receiving the cardiac state parameter provided by the data analysis platform and pushing the cardiac state parameter to the user. In some embodiments, the cardiac state parameter pushing unit is disposed on the wearable part. For example, a display screen is disposed at the pendant 2 of the necklace to display the current working mode and a portion of the key data on the display screen, or a plurality of indicator lights are disposed on the necklace rope 1. When the detection data presents normal condition, the indicator light is green. When the detection data presents abnormal condition, the indicator light is red.

Figure 9:
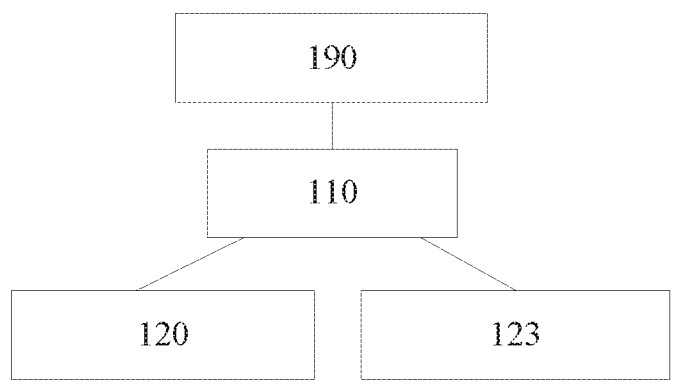
FIG. 9 is a block diagram of a wearable cardiac monitoring device with a body feature collecting function.

As shown in FIG. 9, the wearable cardiac monitoring device of the present disclosure further includes a body feature collection unit 190 for collecting physical characteristics of the user. In some embodiments, the physical characteristics may be user's body temperature data, respiratory frequency, and body surface humidity, blood pressure, etc. The physical characteristics can be selected according to the needs. The body feature collection unit 190 is disposed on the rope of the necklace or in the pendant of the necklace. In addition, other function units for measuring other parameters of the human body, e.g. a skin surface humidity measuring unit and the like, are further added to the wearable cardiac device of the present disclosure. The function units selectively increased in response to the requirements to further increase the functions of the wearable cardiac monitoring device.

Figure 10:
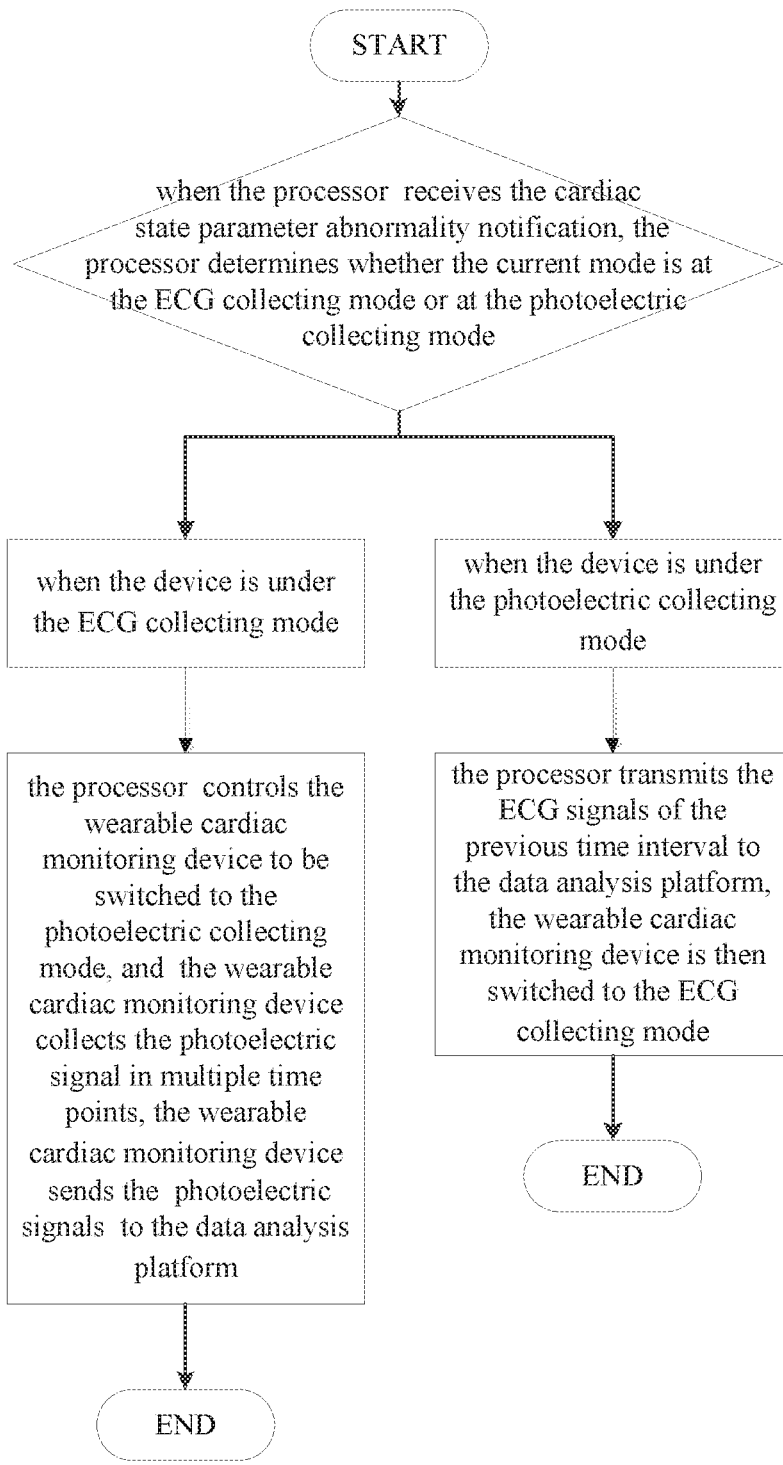
FIG. 10 is a schematic diagram of a method of mode switching of one embodiment of the present disclosure.

As shown in FIG. 10, the processor 110 also switches the working mode based upon the condition of the cardiac state parameter. When the processor 110 receives abnormal notification of the cardiac state parameter sent by the data analysis platform, the processor 110 determines whether the current mode is at the ECG collecting mode or at the photoelectric collecting mode.

When the device is operated under the photoelectric collecting mode, the processor 110 controls the wireless transmission unit to transmit the ECG signals of the previous time interval to the data analysis platform, the wearable cardiac monitoring device is then switched to the ECG collecting mode. In addition, since the user have previously adjusted the state of the wearable cardiac monitoring device, for example, the length of the necklace rope is adjusted, the first electrode 121 is then no longer disposed close to the user's heart, or the second electrode 122 and the third electrode 123 are no longer disposed close to the user's skin. Therefore, the wearable cardiac monitoring device has inability to perform ECG measurement. Therefore, the processor 110 also needs to notify the user to make the wearable cardiac monitoring device stay in an ECG measurable state. The ECG measurable state is that the first electrode 121 is disposed close to the user's heart, and the second electrode 122 and the third electrode 123 are disposed close to the user's skin.

By adopting the switching mode of the above working mode, the processor 110 switch the wearable cardiac monitoring device to another collecting mode to avoid false alarm caused by inaccuracy of the previous collecting mode once the cardiac state parameter analyzed by the data analysis platform is abnormal. The collecting mode is used to compare and supervise each other to ensure the accuracy of the final cardiac state parameters. In addition, when switching, it is necessary to ensure that the data analysis platform can obtain the signals of the two collecting modes within a certain period of time, to simultaneously analyze and compare.

Figure 11:
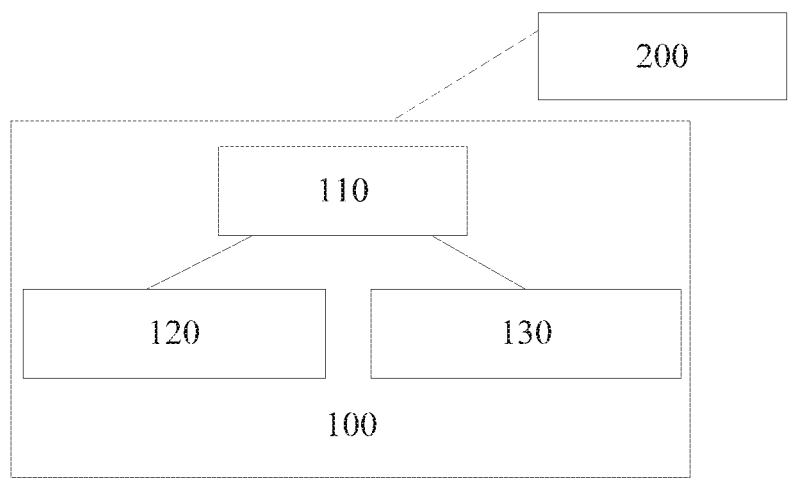
FIG. 11 is a block diagram of a cardiac monitoring system of one embodiment of the present disclosure.

As shown in FIG. 11, one embodiment of the present disclosure further provides a cardiac monitoring system including the wearable cardiac monitoring device 100 and a data analysis platform 200. The data analysis platform is configured to generate cardiac state parameters in response to the ECG signal and/or the photoelectric signal.

The cardiac monitoring system of the present disclosure adopts the architecture of the Internet of Things, and in combination with the two methods of ECG monitoring and photoelectric detection. Therefore, the time latency caused by inability of obtaining the cardiac detecting result in real time is then removed, even the dynamic electrocardiogram only provide real time detection. Once the cardiac state parameter is abnormal, the user can know in time.

Figure 12:
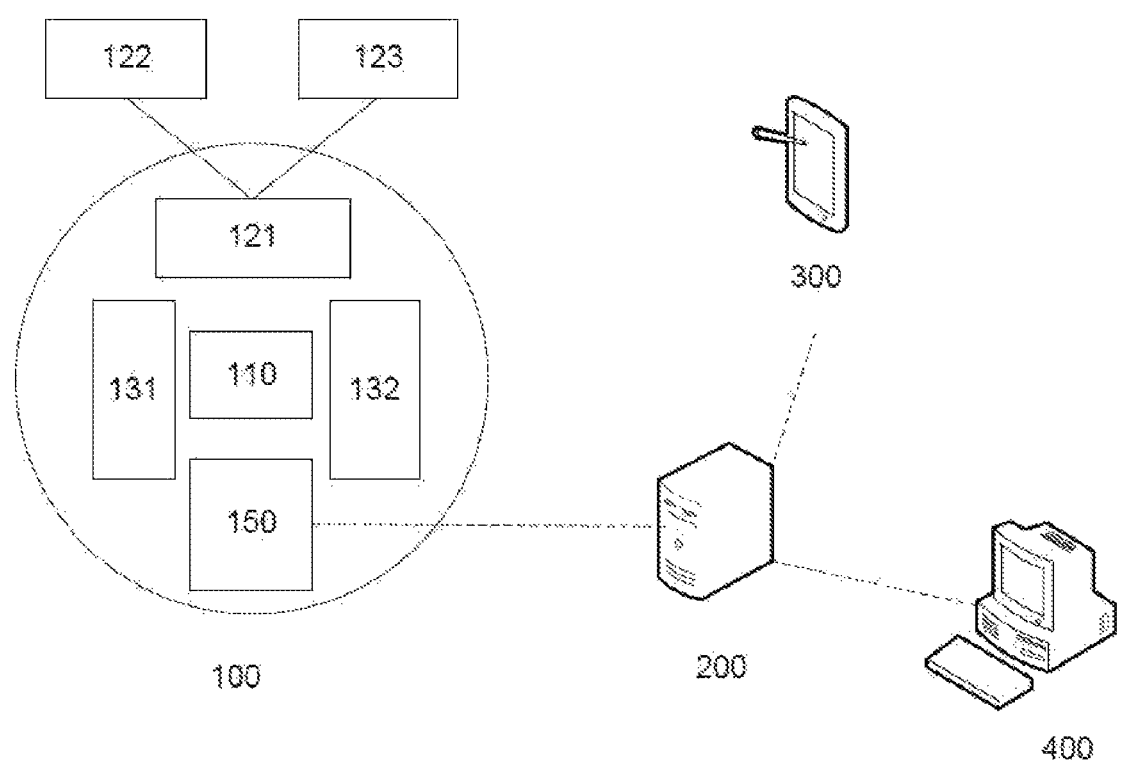
FIG. 12 is a block diagram of a cardiac monitoring system of another embodiment of the present disclosure.

As shown in FIG. 12, the cardiac monitoring system further includes a user terminal 300 and/or a medical institution management platform 400. The data analysis platform 200 is further configured to send the cardiac state parameter to the user terminal 300 and/or the monitoring terminal. The data analysis platform 200 includes a cloud server, and the user terminal 300 includes a user's mobile phone, a tablet computer, or a personal computer. The medical institution management platform 400 includes a server of a hospital or a rescue center or a doctor's personal computer, etc. The user terminal 300 performs data interaction through the data analysis platform 200 and the wearable cardiac monitoring device 100, or the user terminal 300 directly performs data interaction with the wearable cardiac monitoring device 100 through the wireless network. The user terminal 300 further undertakes some task of data display and reception of the user instruction.

In this way, the user's terminal 300 and the medical institution management platform 400 are able to directly check the data of the user's electrocardiogram and heart rate. If the doctor is aware of an abnormality of the cardiac state parameter appeared on the medical institution management platform 400, the doctor can contact the user. When the abnormality of the cardiac state parameter is detected in the user terminal 300 and the user has no response, the emergency call can be made to avoid inability of treating the emergency situation happened on the user.

Figure 13:
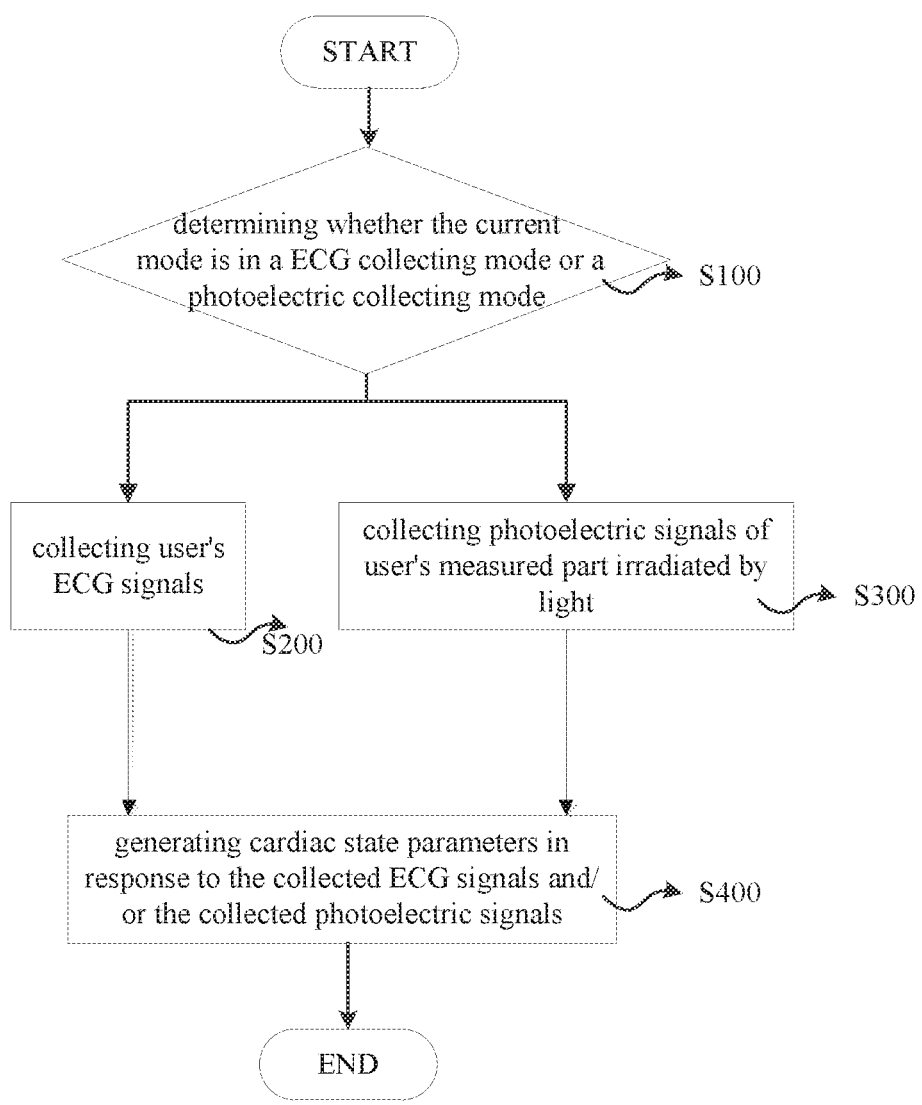
FIG. 13 is a flow chart of a cardiac monitoring method of one embodiment of the present disclosure.

As shown in FIG. 13, the present disclosure further provides a cardiac monitoring method implemented by the cardiac monitoring system. The cardiac monitoring method comprises the following steps.

S100: determining whether the current mode is in a ECG collecting mode or a photoelectric collecting mode;

S200: collecting user's ECG signals in the ECG collecting mode;

S300: collecting photoelectric signals of user's measured part irradiated by light in the photoelectric collecting mode;

S400: generating cardiac state parameters in response to the collected ECG signals and/or the collected photoelectric signals.

Figure 14:
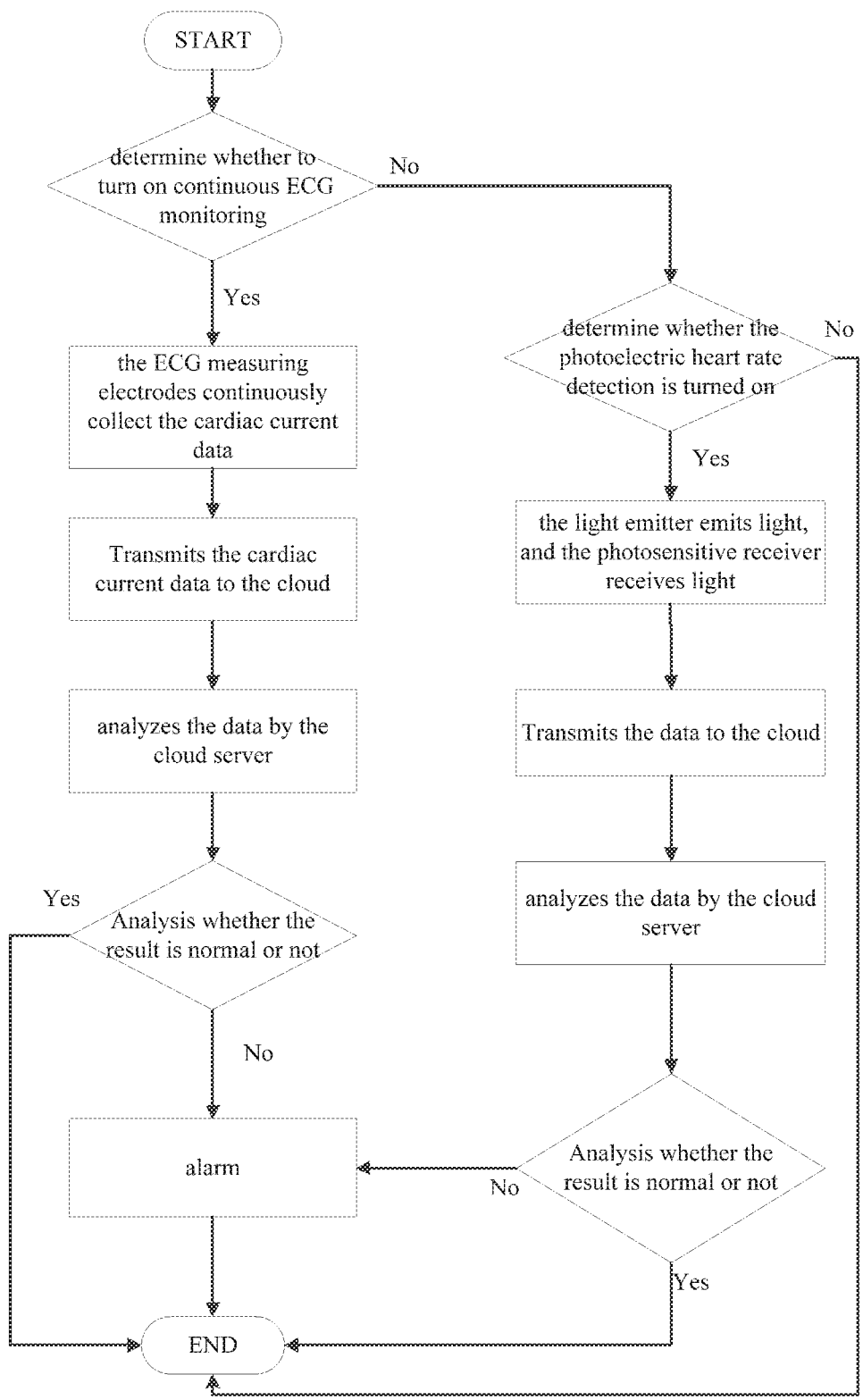
FIG. 14 is a flow chart of a cardiac monitoring method of another embodiment of the present disclosure.

As shown in FIG. 14, FIG. 14 shows a flow chart of a cardiac monitoring method of one embodiment of the present disclosure. In this embodiment, there are three modes including an off mode, an ECG collecting mode, and a photoelectric collecting mode. The method includes the following steps.

Firstly, determine whether to activate continuous ECG monitoring. If the continuous ECG monitoring is activated, the ECG collecting mode is entered, and the three electrodes continuously collect the cardiac current data.

Transmit the cardiac current data to the data analysis platform in cloud, and analyzes the data by the data analysis platform in cloud.

Analyze whether the result is normal or not. The current process is terminated when the analysis result is normal. It is necessary to send out an alarm signal when the analysis result is not normal.

If the continuous ECG monitoring is not activated, then determine whether the photoelectric heart rate detection is activated;

If the photoelectric heart rate detection is activated, the photoelectric collecting mode is entered. The light emitter emits light, and the photosensitive receiver receives light.

Transfer data to the data analysis platform in cloud, and analyze the data by the cloud server.

Analysis whether the result is normal or not. The current process is terminated when the analysis result is normal. It is necessary to send out an alarm signal when the analysis result is not normal.

If the photoelectric heart rate detection is not activated, it means that the current process is in the off mode. The current process is terminated directly.

The above-mentioned modes, including off mode, ECG collecting mode, and photoelectric collecting mode, are examples. In practice, the default configuration mode is an on mode and an off mode, is canceled. Moreover, other mode including body temperature detection mode etc. is further added and, all of the added modes are within the scope of protection of the present disclosure.

The measurement method of ECG is more accurate, and the timeliness is not high. It takes a certain time to continuously perform measurement to get a more accurate ECG index. The photoelectric method is faster in performing measurement, which can meet the requirements of timeliness, but the photoelectric method is easily interfered by light of environment, user skin cleanliness and other factors. Thus, the measurement is not quite accurate.

Therefore, the cardiac monitoring method of the present disclosure includes the methods of photoelectric detection and ECG measurement, which allow the user to select different measurement methods according to needs. When more accurate measurement data is needed, the ECG measurement mode is kept functioning. When heart rate data needs to be obtained immediately, the photoelectric measurement mode is then entered. Therefore, the method of the present disclosure includes two advantages which are timeliness and accuracy, and fully meet the user's usage requirements.

Figure 15:
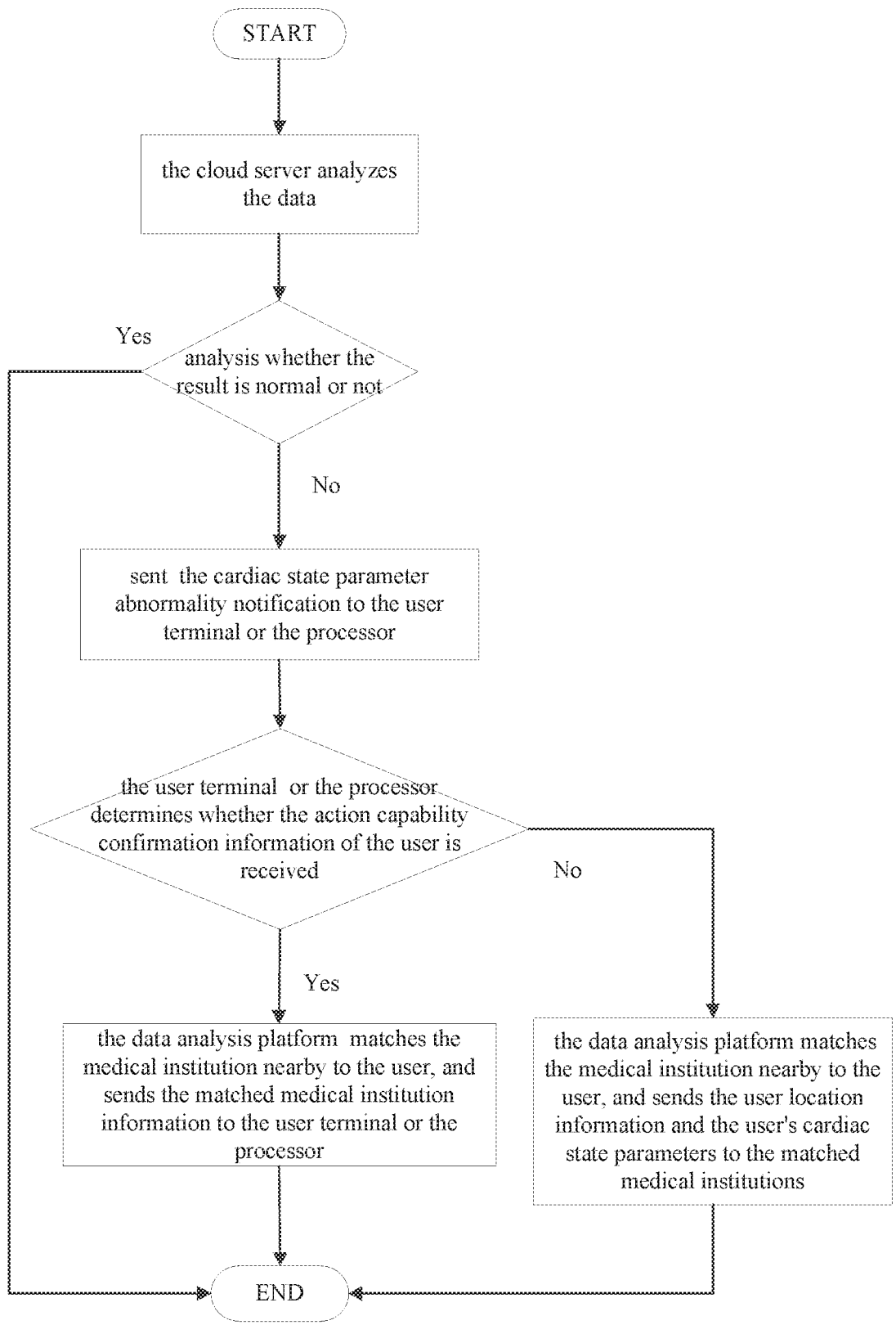
FIG. 15 is a flow chart of the processing procedure during abnormal condition occurred in cardiac monitoring of one embodiment of the present disclosure.

As shown in FIG. 15, the processing method for abnormality of the cardiac state parameter obtained by the cardiac monitoring method of the present disclosure includes the following steps.

The cloud server analyzes the data to obtain the cardiac state parameter. When the analysis result is abnormal, the abnormality notification of the cardiac state parameter is sent to the user terminal 300 or the processor 110 of the wearable cardiac monitoring device 100.

The user terminal 300 or the processor 110 determines whether the action capability confirmation of the user is received.

If the user's action capability confirmation is received, it indicates that the user still has the action and consciousness ability to go to the doctor by himself. The data analysis platform 100 matches the medical institution nearby the user, and sends the matched medical institution information to the user terminal 300 or the processor 110.

If the user's action capability confirmation is not received, it indicates that the user may not have the action and consciousness ability to go to the doctor himself. The data analysis platform 100 matches the medical institution nearby to the user, and sends the user location information and the user's cardiac state parameters to the matched medical institutions, which facilitates the medical institutions to go to rescue. In many ways, the method of the present disclosure significantly ensures the safety of the users.

The cardiac monitoring system and method provided by the present disclosure has the following advantages.

The present disclosure provides a technical solution for monitoring the cardiac status real time and being easy to wear. The technical solution is implemented in a combination with electrocardiogram and photoelectric method for performing cardiac status monitoring. The electrocardiogram monitoring has high accuracy, and the photoelectric monitoring has a fast speed. Various cardiac monitoring methods are selected according to the need. The device has both advantages of accuracy and real-time. The device is integrated in the wearing parts. The size of the device is compact. The device is easy to wear. The device can execute the cardiac monitoring anytime and anywhere, without bringing the carrying burden of users, and improve user's usage experience.

The above is a further detailed description of the present disclosure in connection with the specific preferred embodiments, and the specific embodiments of the present disclosure are not limited to the description. For ordinary technicians in the technical field of the invention, several simple deductions or substitutions can be made without departing from the concept of the invention, which should be regarded as belonging to the scope of protection of the invention.

What is claimed is:

1. A wearable cardiac monitoring device, comprising:
    a processor;
    an electrocardiogram (ECG) signal collecting unit;
    a photoelectric signal collecting unit;
    a power source configured to provide power to the processor, the ECG signal collecting unit and the photoelectric signal collecting unit simultaneously; and
    a wireless transmission unit,
    wherein the processor determines whether the current mode is at a ECG collecting mode or a photoelectric collecting mode; wherein the ECG signal collecting unit collects user's ECG signals in the ECG collecting mode, and the photoelectric signal collecting unit collects photoelectric signals of the user's measured part under the illumination of light in the photoelectric collecting mode,
    wherein when the processor receives a notification of abnormal cardiac status parameters transmitted by a data analysis platform, the processor determines whether the current mode is the ECG collecting mode or the photoelectric collecting mode;
    wherein when the wearable cardiac monitoring device is under the photoelectric collecting mode, the processor controls the wireless transmission unit to transmit the ECG signals of the previous time interval to the data analysis platform, the wearable cardiac monitoring device is then switched to the ECG collecting mode, and the wearable cardiac monitoring device notifies the user that the wearable cardiac monitoring device is under the ECG collecting mode.

2. The wearable cardiac monitoring device of claim 1, wherein the ECG signal includes user's cardiac current, and the ECG signal collecting unit includes a first electrode close to user's heart in the ECG collecting mode and a second electrode and third electrode close to user's skin during the ECG collecting mode, wherein the first electrode, the second electrode and the third electrode form a cardiac current measuring circuit.

3. The wearable cardiac monitoring device of claim 2, wherein the processor, the ECG signal collecting unit, the photoelectric signal collecting unit and the power source are all installed in a wearable part;
    wherein the wearable part includes a necklace rope, the first electrode is installed at a first position of the necklace rope, the second electrode and the third electrode are installed at second position and third position of the necklace rope respectively, and wherein the second position and third position are respectively distant from the first position with a same distance;

when the user wears the necklace rope, the second position and third position are respectively close to a side of the user's neck, and the first position, in the ECG collecting mode, is close to user's heart position.

4. The wearable cardiac monitoring device of claim 3, wherein a conductive ring is disposed in the necklace rope, and the necklace rope is also connected to a pendant, wherein the processor, the ECG signal collecting unit, the photoelectric signal collecting unit and the power source are disposed in the pendant, and the first electrode is electrically connected, through the conductive ring, to the second electrode and the third electrode.

5. The wearable cardiac monitoring device of claim 4, wherein a length adjustment button is disposed at the position where the necklace rope is connected to the pendant; wherein when the length adjustment button is at an adjustment state, the length of the necklace rope is adjustable.

6. The wearable cardiac monitoring device of claim 4, wherein a mode selection button is disposed in the pendant;
wherein when the mode selection button is switched to a first mode and is detected by the processor, the ECG collecting mode is then determined by the processor;
when the mode selection button is switched to a second mode and is detected by the processor, the photoelectric collecting mode is then determined by the processor;
when the mode selection button is switched to a third mode and is detected by the processor, the sleep mode is then determined by the processor.

7. The wearable cardiac monitoring device of claim 6, wherein when the power capacity of the power source is determined, by the processor, smaller than a first pre-defined threshold and greater than a second pre-defined threshold, the photoelectric collecting mode is then activated and the processor controls photoelectric collecting unit to collecting the photoelectric signals in response to pre-defined collecting intervals of photoelectric signal;
when the power capacity of the power source is determined, by the processor, smaller than the second pre-defined threshold, the sleep mode is then activated by the processor.

8. The wearable cardiac monitoring device of claim 1, wherein the photoelectric signal is reflected light of the user's measured part under the illumination of light in the photoelectric collecting mode, wherein the photoelectric signal collecting unit is close to user's skin in the photoelectric collecting mode, and the photoelectric signal collecting unit comprises:
a light emitter configured for emitting light to surface of user's skin;
a photosensitive receiver configured for receiving the reflected light reflected by the user's measured part.

9. The wearable cardiac monitoring device of claim 1, wherein the wireless transmission unit further configured to send the ECG signal and/or the photoelectric signal to the data analysis platform, wherein the data analysis platform is configured to generate cardiac state parameters in response to the ECG signal and/or the photoelectric signal, wherein the cardiac state parameters includes ECG indicator data and heart rate data.

10. The wearable cardiac monitoring device of claim 9, wherein the device further comprises an alarm unit configured to push an alarm signal to the user when the cardiac monitoring device receives the abnormal notification of the cardiac state parameters transmitted by the data analysis platform;
a user information input unit configured to receive user's action capability confirmation information when the cardiac monitoring device receives the abnormal notification of the cardiac state parameters transmitted by the data analysis platform.

11. The wearable cardiac monitoring device of claim 10, wherein further includes a locating unit configured to automatically locate user's position information and to transmit the user's position information to the data analysis platform when the cardiac monitoring device receives the abnormal notification of cardiac state parameters transmitted by the data analysis platform.

12. The wearable cardiac monitoring device of claim 11, wherein the device further includes a display unit configured to display information of a medical institution, matched and provided by the data analysis platform, nearby to the users location, when the wearable cardiac monitoring device receives the abnormal notification of cardiac state parameters transmitted by the data analysis platform, and the user information input unit receives the user's action capability confirmation information.

13. A cardiac monitoring system, comprising:
a wearable cardiac monitoring device, comprising:
a processor;
an electrocardiogram (ECG) signal collecting unit;
a photoelectric signal collecting unit;
a power source configured to provide power to the processor, the ECG signal collecting unit and the photoelectric signal collecting unit simultaneously; and
a wireless transmission unit,
wherein the processor determines whether the current mode is at a ECG collecting mode or a photoelectric collecting mode; wherein the ECG signal collecting unit collects user's ECG signals in the ECG collecting mode, and the photoelectric signal collecting unit collects photoelectric signals of the user's measured part under the illumination of light in the photoelectric collecting mode; and
a data analysis platform, wherein the data analysis platform is configured to generate cardiac state parameters in response to the ECG signal and/or the photoelectric signal,
wherein when the processor receives a notification of abnormal cardiac status parameters transmitted by the data analysis platform, the processor determines whether the current mode is the ECG collecting mode or the photoelectric collecting mode;
wherein when the wearable cardiac monitoring device is under the photoelectric collecting mode, the processor controls the wireless transmission unit to transmit the ECG signals of the previous time interval to the data analysis platform, the wearable cardiac monitoring device is then switched to the ECG collecting mode, and the wearable cardiac monitoring device notifies the user that the wearable cardiac monitoring device is under the ECG collecting mode.

14. The cardiac monitoring system of claim 13, further including a user terminal and/or a medical institution terminal, wherein the data analysis platform is further configured to transmit the cardiac state parameters to the user terminal and/or the medical institution terminal.

15. The cardiac monitoring system of claim 14, wherein the data analysis platform transmits a notification of the abnormal cardiac state parameters to the user terminal, when the notification of the abnormal cardiac state parameters is determined by the data analysis platform;

the user terminal displays the cardiac state parameters, and the information of the nearby medical institution, matched and provided by the data analysis platform, is displayed by the user terminal, when the user terminal receives the abnormal notification of the cardiac state parameters transmitted by the data analysis platform and receives the user's action capability confirmation information within a predetermined time;

the user terminal returns a notification of an user abnormal state to the data analysis platform, when the user terminal receives the abnormal notification of the cardiac state parameters transmitted by the data analysis platform and does not receive the user's action capability confirmation information within a predetermined time;

the data analysis platform matches the medical institution nearby to the user, and transmits the user's position information and user's cardiac state parameters to the matched medical institution, after the data analysis platform receives the notification of the abnormal user state.

16. A method of cardiac monitoring, implemented by a cardiac monitoring system, comprising:
a wearable cardiac monitoring device, comprising:
  a processor;
  an electrocardiogram (ECG) signal collecting unit;
  a photoelectric signal collecting unit;
  a power source configured to provide power to the processor, the ECG signal collecting unit and the photoelectric signal collecting unit simultaneously; and
  a wireless transmission unit, wherein the processor determines whether the current mode is at a ECG collecting mode or a photoelectric collecting mode; wherein the ECG signal collecting unit collects user's ECG signals in the ECG collecting mode, and the photoelectric signal collecting unit collects photoelectric signals of the user's measured part under the illumination of light in the photoelectric collecting mode; and a data analysis platform, wherein the data analysis platform is configured to generate cardiac state parameters in response to the ECG signal and/or the photoelectric signal, the method comprising steps of:

determining whether the current mode is in a ECG collecting mode or a photoelectric collecting mode;

collecting user's ECG signals in the ECG collecting mode;

collecting photoelectric signals of user's measured part irradiated by light in the photoelectric collecting mode;

generating cardiac state parameters in response to the collected ECG signals and/or the collected photoelectric signals;

when the processor receives a notification of abnormal cardiac status parameters transmitted by the data analysis platform, determining whether the current mode is the ECG collecting mode or the photoelectric collecting mode;

when the wearable cardiac monitoring device is under the photoelectric collecting mode, controlling the wireless transmission unit to transmit the ECG signals of the previous time interval to the data analysis platform, the wearable cardiac monitoring device is then switched to the ECG collecting mode, and the wearable cardiac monitoring device notifies the user that the wearable cardiac monitoring device is under the ECG collecting mode.

* * * * *